Figure 1:
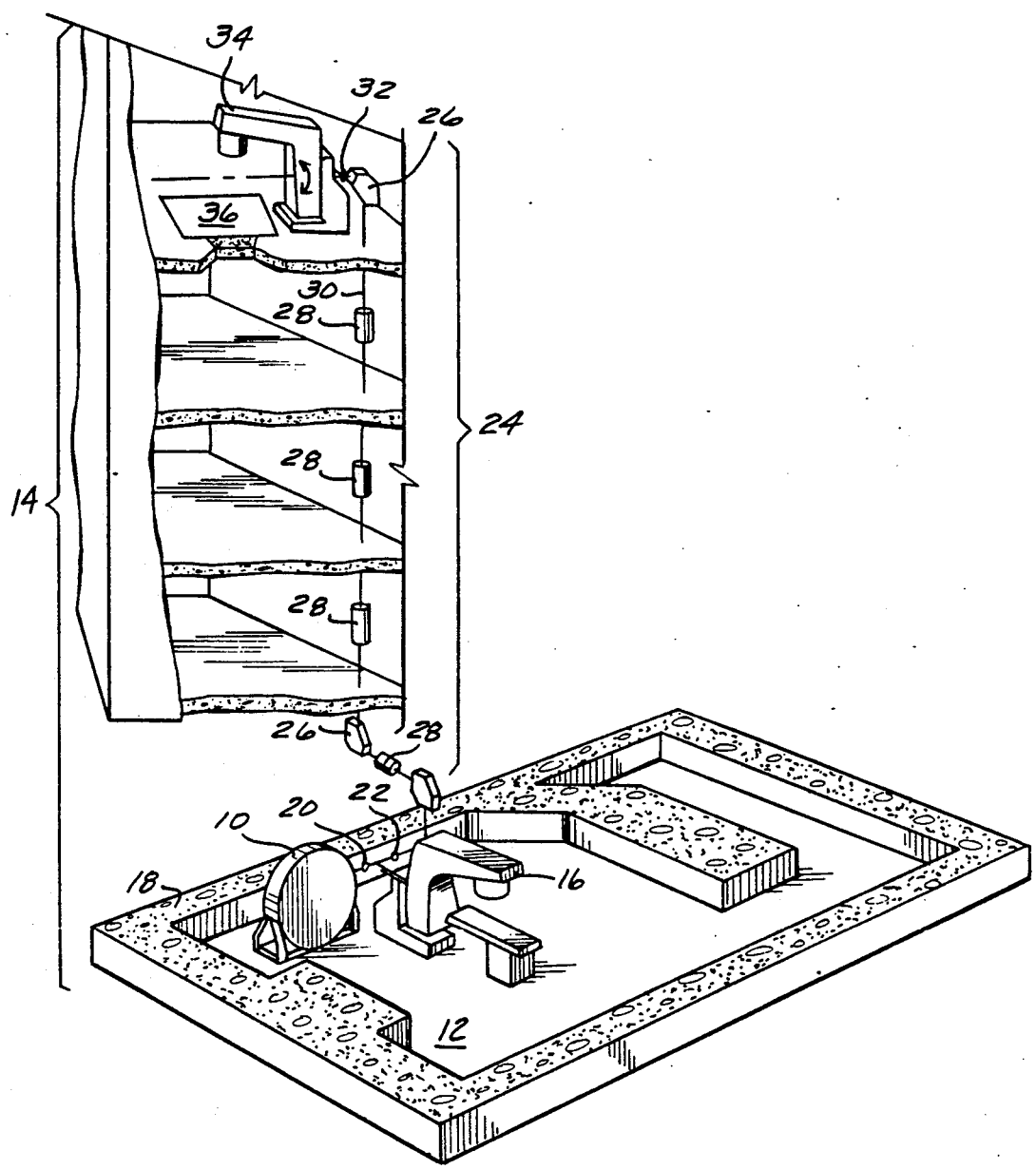

United States Patent [19]

Bronn

[11] Patent Number: 5,190,516
[45] Date of Patent: Mar. 2, 1993

[54] METHOD INTRAOPERATIVE ELECTRON BEAM RADIOTHERAPY USING REMOTELY LOCATED BEAM GENERATOR

[76] Inventor: Donald G. Bronn, 4901 Susans Way, Bloomfield Hills, Mich. 48013

[21] Appl. No.: 540,453

[22] Filed: Jun. 19, 1990

Related U.S. Application Data

[60] Continuation of Ser. No. 267,573, Nov. 8, 1988, abandoned, which is a division of Ser. No. 911,135, Sep. 24, 1986, abandoned.

[51] Int. Cl.$^5$ .............................................. A61N 5/10
[52] U.S. Cl. ........................................ 600/1; 128/898
[58] Field of Search .......................... 250/492.1, 492.3; 128/897, 898; 600/1, 2; 606/32-34

[56] References Cited

U.S. PATENT DOCUMENTS

| | | | |
|---|---|---|---|
| 2,018,599 | 10/1935 | Brasch | 250/492.3 |
| 2,741,704 | 4/1956 | Trump et al. | 250/492.3 |
| 3,547,074 | 4/1967 | Herschfeld | 250/492.1 |
| 3,555,332 | 10/1967 | Schroeder et al. | 250/492.3 |
| 3,842,279 | 10/1974 | Schumacher | 250/492.3 |

FOREIGN PATENT DOCUMENTS 208030 3/1984 Fed. Rep. of Germany ... 250/492.1

OTHER PUBLICATIONS

"Intraoperative Irradiation" by Gunderson et al; Cancer vol. 49, No. 11 (1982) pp. 2259-2266.
"Radiation Therapy and Surgery" by Tepper et al. Cancer Treatment Symposia vol. 1, 1984.
"Characteristics of an M22 Medical Microtron 6-MV photon beam" by George; Med Phy 11 (6) Nov.-Dec. 1984 pp. 862-865.
"Clinical Experience with the 22-MeV Microtron at the National Cancer Center Hospital" by Egawa et al.; Jpn. J. Clin. Oncol, 1984 14(4) pp. 613-622.
"A 22 MeV Microtron for Radiation Therapy" by Svensson et al.; Acta Radiologicer Therapy Physics Biology 16(1977) Fusc 2 Apr. 1 pp. 145-156.

Primary Examiner—David M. Shay
Attorney, Agent, or Firm—John R. Benefiel

[57] ABSTRACT

A microtron-generated electron beam may be selectively routed through an extended electron beam transport system to a remotely located intraoperative radiotherapy (IORT) facility. The beam current is preferably limited to a value (e.g., 100 nanoamperes) so as to avoid the necessity for overly extensive shielding along the beam transport system and at the remote therapy site while yet being sufficiently high to provide effective treatments. The intraoperative radiotherapy gantry and treatment head are preferably optimized for just this purpose and is thus considerably simplified over conventional electron/photon therapy gantries and treatment heads. In a method of intraoperative radiotherapy, different energy level beams are capable of being generated, a low level beam transported over a light shielded system to a conventional operating suite, with a high energy beam transported to a conventional radiotherapy site. In addition, the electron beam output of the microtron may be utilized on a time-shared basis with a plurality of similar and/or conventional electron/proton therapy systems.

3 Claims, 2 Drawing Sheets

METHOD INTRAOPERATIVE ELECTRON BEAM RADIOTHERAPY USING REMOTELY LOCATED BEAM GENERATOR

This application is a continuation, of application Ser. No. 07/267,573, which was filed on Nov. 8, 1988 and which is now abandoned, which is a division of application Ser. No. 06/911,135, filed Sep. 24, 1986, now abandoned.

This invention is generally related to radio therapy systems of the type which include intraoperative radiotherapy (IORT) facilities. It is particularly directed to such a system where the IORT facility is remotely located (e.g., in an upper floor operating room site) from the electron beam generating devices and other more conventional radiotherapy facilities which require heavy and extensive radiation shielding High energy electron beams have been used for some time now in various types of radiotherapy (e.g., to destroy cancerous tissues at selected body locations). The electron beams may be used directly as in electron beam radiotherapy or indirectly to produce photons (e.g., by directing the electron beam to suitable targets) which are, in turn, directed onto desired patient sites.

Various types of electron beam generators have been used for these purposes. However, they all typically involve relatively large, heavy and massive pieces of equipment which inherently produce high levels of ambient radiation which must therefore be physically located in heavily shielded facilities (e.g., typically on the lowest or basement level of a multi-story building). Furthermore, the relatively high electron beam energy/currents utilized for photon radio therapy also require heavy radiation shielding to be used throughout the beam transport/delivery system (including the treatment gantry and treatment head) so as to protect operating staff, doctors, nurses, etc.,—and even the non-treated portions of the patient.

The microtron type of electron beam accelerator has been particularly favored by some as the electron beam generator for such systems. In part, the microtron generator has been favored because its output electron beam can relatively easily be provided at selected discrete energy levels at a fixed output port site while also insuring a relatively narrow energy spread (e.g., ±50 KeV) within a beam of electrons having relatively high levels (e.g., selectable at discrete values between 3 to 22 or more MeV). For example, such microtrons are commercially available from Scanditronix Inc. under model designations MM14, MM22 and MM50.

Although, in the past, electron/photon beam radio therapy has typically been performed by transmitting a shaped beam of such radiation through external body surfaces to the desired treatment site, a newer technique is now on the horizon which offers considerable possible advantage. It is known as "intraoperative radiotherapy" (IORT) and involves a more direct application of the treatment beam directly to an internal treatment surface which has been exposed temporarily during the course of a surgical procedure. For example, surgical procedures might be used to open the patient's body and perhaps even partially remove some cancerous tissue. At the same time, any possibly remaining cancerous tissue may be almost directly accessible for radiotherapy. If so, then the desired radiotherapy beam can be very selectively applied directly to the desired treatment site. This not only minimizes unwanted exposure to normal body tissues, it also insures delivery of a relatively higher radiotherapy dose rate and dose per fraction to the desired treatment site.

There are many potential advantages to IORT which investigators would like to explore and for which there is gathering considerable further interest. For example, one published report ("Radiation Therapy and Surgery" by Tepper et al, Cancer Treatment Symposia, Volume 1, 1984, pp 111–117) notes that experimentation with IORT techniques might better determine whether the potential advantages are actually realized. However, Tepper et al note that IORT is currently limited due to the fact that electron beam therapy units are not presently available in operating room suites. Tepper et al advocate the allocation of sufficient resources to permit the installation of a dedicated electron beam generator and IORT facility directly in the operating room.

Intraoperative radiotherapy (IORT) thus has gained considerable interest recently with favorable reports promoting its therapeutic value in minimizing dose to normal tissues and maximizing dose to the tumor. However, its true therapeutic role is yet to be determined and will require large scale trials. Although a number of institutions are using IORT, patient accrual has been limited due to technical considerations. There are currently four methods of IORT:

1. Treatment by a linear accelerator in the radiotherapy suite whereby patents are transported between the operating room and the radiotherapy facility under general anesthesia in the middle of surgery. This is extremely time consuming and potentially risky to the patient in terms of prolonged anesthesia and possibility of infection. Logistically, this is also quite disruptive to the operating room and radiotherapy personnel and requires pretreatment cleaning and sterilization of the access hallways and radiotherapy suite and equipment. Patents must be preselected for this therapy in advance and usually require a second operative procedure for the intraoperative therapy. Preselection limits the availability of IORT.

2. Establishment of an operative theatre in the radiotherapy facility is expensive and inconvenient for the operating room personnel and the radiotherapy facility. A prolonged operative procedure prior to IORT monopolizes the radiation treatment suite and interferes with the regular use of that treatment unit throughout the period of the operation. This is highly cost ineffective and discourages patient accrual. Furthermore, performance of an operation away from the operative floor taxes the resources of both the anesthesia and surgical personnel and who are isolated from the general operative facilities and support systems. Both surgeons and anesthesiologists strongly resist performing complete operations away from the operative floor. As a result, patents will most likely undergo the primary surgery in the regular operative facilities and have a second limited operative procedure in the radiotherapy operating room. Thus, the patient is subjected to a second operative procedure with associated risk of a second general anesthesia. Preselection is again required.

3. Placement of a linear accelerator in the operating suite on the surgical floor is a logical alternative which eliminates preselection and facilitates patient treatment, thus making IORT more available.

However, an appropriate high energy linear accelerator with electron beam capability requires extensive radiation shielding which is very expensive and may not be structurally feasible in existing structures. Full utilization of a dedicated linear accelerator on the operating floor is not achieved because, during a regular operating day, the unit will be used at most three or four times for several minutes, and use of the machine only once a day is more likely on the average. Therefore, a dedicated high energy linear accelerator in the operating suite is not cost-effective because its use is strictly limited to the operating suite for those patients who are found to be appropriate candidates after lengthy operating procedures.

A dedicated linear accelerator on the operating floor is also costly in terms of valuable space utilization within the operating complex. The mechanical hardware, with associated regular maintenance, places additional burdens in terms of maintaining a clean and sterile environment on the operating floor.

4. An orthovoltage treatment unit (250 or 300 kVp) in the operating suite can be achieved with minimal shielding requirements because of the low energy penetration of the unit. These units are much less expensive to install in operating rooms. However, they have inferior depth-dose characteristics making them impractical for treatment of lesions greater than 4 cm in thickness. They also provide an increased dose to bones, and they have a low dose rate resulting in long treatment times for the patient under anesthesia and isolated in the operating suite during intraoperative irradiation.

Although these prior approaches to the IORT problem each remain burdened by many practical problems, I have now discovered a radiation therapy system of novel configuration which largely avoids such disadvantages. For example, although the electron beam output from a linear accelerator includes rather broad energy ranges and is thus difficult to transport significant distances, the electron beam output beam from a microtron has a much narrower range of energies and may thus be routed more conveniently and economically through less complex beam deflectors, focusers and beam steering devices (each of which is individually of conventional and known design). Furthermore, if a microtron (or equivalent) electron beam source is employed, it is also possible to control the output beam current to a value which is high enough to provide effective electron beam therapy while yet not so high as to require overly extensive radiation shielding along the beam transport/utilization route.

These and other factors have led to a novel radiation therapy system configuration which permits cost effective time-shared routing of an electron beam to a remote operating suite where it may be most conveniently and effectively used for IORT. A remote control console directly in the operating suite is used to communicate with the main microtron system control so as to selectively route the electron beam output into an extended beam transport system which includes suitable beam deflection, focusing and steering units distributed therealong. In the preferred embodiment, such beam transport devices are controlled by selection of preset d.c. power supplies which are selected corresponding to a selected energy level output from the microtron (e.g., so as to properly deflect, focus and steer an electron beam of that selected energy through the extended transport system).

In the exemplary embodiment a 22.5 MeV therapy microtron produces an electron beam which serves two treatment stations in the radiotherapy facility with conventional photons and electrons. A third beam pipe is selectively utilized to transport an electron beam to a treatment gantry in the operating suite on the surgical floor. The IORT gantry in the operating suite may be modified for electron use only (thus effecting a great economy in bulk, weight, etc.) with different discrete electron beam energies from 3 to 22 MeV (each having only a narrow energy spread on the order of $\pm 50$ KeV). Operating room space utilized by the IORT gantry is greatly reduced because the beam is generated at the microtron. Thus, the treatment gantry can be reduced considerably in size as compared to a linear accelerator treatment head which must also house part of the energy generating system. In addition, a mechanically clean environment can be maintained on the operating floor since the beam generating microtron is located in the remote radiation therapy facility.

The cost of the exemplary "triple" beam system embodiment is roughly equivalent to two conventional high energy linear accelerators. The IORT part of the system, which includes the long distance beam transport pipe to the operating suite, is less expensive than an isolated linear accelerator with less technical capability. (And this does not even take into account the cost of shielding requirements which are greater for the linear accelerator in the operating suite and may not always be structurally feasible in existing structures.)

Shielding requirements for the extended electron beam transport system along the beam pipe and in the operating suite are minimized because, in the electron therapy mode, the output beam preferably is limited within the basic microtron to about 100 nanoamperes. For example, the extended beam transport tube may be an aluminum tube having only about 80 mm (3.25 inches) of lead shielding wrapped thereabout. If located outside the building for part of the transport distance, even less shielding (e.g., none) may be required. This minimized shielding cannot be achieved with a conventional linear accelerator because of the higher energy necessarily generated at the gantry site which is in the operating suite. Or if the linear accelerator beam is transported over any distance, the wide band energy output implies costly beam transport structures including extensive radiation shielding.

Cost-effectiveness of the system is enhanced because the beam is used routinely on a full time basis in the radiotherapy facility for conventional photon and electron therapy. The beam is sent to the operating floor only for a few minutes when needed for IORT electron therapy There is minimal disruption of routine activities by operating or radiotherapy personnel during this process.

Since this system utilizes the high energy capabilities of the microtron without the associated problems related to high energy generation in the operating suite, it is therefore possible to have the widest spectrum of electron energy levels (e.g., up to 22 MeV) which permits adequate irradiation of lesions as thick as 7 cm. Dose rate can also be high (e.g , 1000 rads/minute) which permits very rapid treatment times. A typical dose of 2000 rads in IORT can be administered in two minutes The anesthetized patent is therefore isolated for a minimum amount of time reducing intraoperating risk.

The extended electron beam transport system may, for example, include 90° deflection magnets (e.g., for directing the beam upward in a typical layout where the operative suite is located several stories (40-60 feet) above the radiotherapy facility). Beam focus is maintained by quadrupole triplets distributed appropriately along the beam transport system and beam position adjustment in both coordinates is achieved by six steering magnets similarly distributed therealong. Precision d.c. power supplies are pre-programmed for each energy setting, maintaining the correct field conditions for each of the beam transport line elements Radiation field symmetry specifications can be conventionally maintained by a servo system which senses and compares signal levels in both the longitudinal and transverse fields and corrects beam spot position by regulating conventional rotating gantry steering coils Depth dose, surface dose, electron field size, dose rate, and gantry angles may be optimized for IORT in this system.

Evaluation of the true potential of IORT requires a technical system which makes this modality practical and convenient for the surgeon, radiation oncologist and patient alike This electron beam transport system is a practical and economic solution which facilitates utilization and promotes patient accrual without the associated risks of patient transportation, prolonged anesthesia, and preselection requiring a second operative procedure.

Some advantages and features provided by the exemplary embodiment are as follows:

1. Allows for intraoperative irradiation in the operating suite on the operating floor without disrupting routine radiotherapy activities and treatment in the radiotherapy area.
2. Beam transportation of about 100 nanoamperes from the microtron to the operating suite allows for minimal shielding, making it structurally feasible to provide adequate shielding for the electron beam.
3. Surgery and anesthesiology personnel are not disrupted for IORT procedures.
4. Radiation therapy equipment is not monopolized during surgical procedures prior to IORT.
5. Clean environment can be maintained in the surgical suites because the high energy generator, with its dirty motor room, is not on the same floor.
6. Valuable operating room space is preserved by using a smaller treatment head because the energy generator is not part of treatment gantry.
7. No pretesting of the beam is necessary in the operating room because the beam is preferably tested in the radiotherapy facility before it is directed to the IORT unit.
8. Widest spectrum of energy levels are possible with high dose rates since the generator is not on the same floor.
9. Patient selection is enhanced because rapid and immediate decisions can be made during the operation regarding the suitability of a patient for IORT. This eliminates preselection and the need for a second operation procedure for IORT.
10. Risks associated with intraoperative patient transportation and prolonged anesthesia are eliminated.
11. System promotes accessiblity of IORT and, therefore, provides many more patients with the opportunity of IORT.

Figure 2:
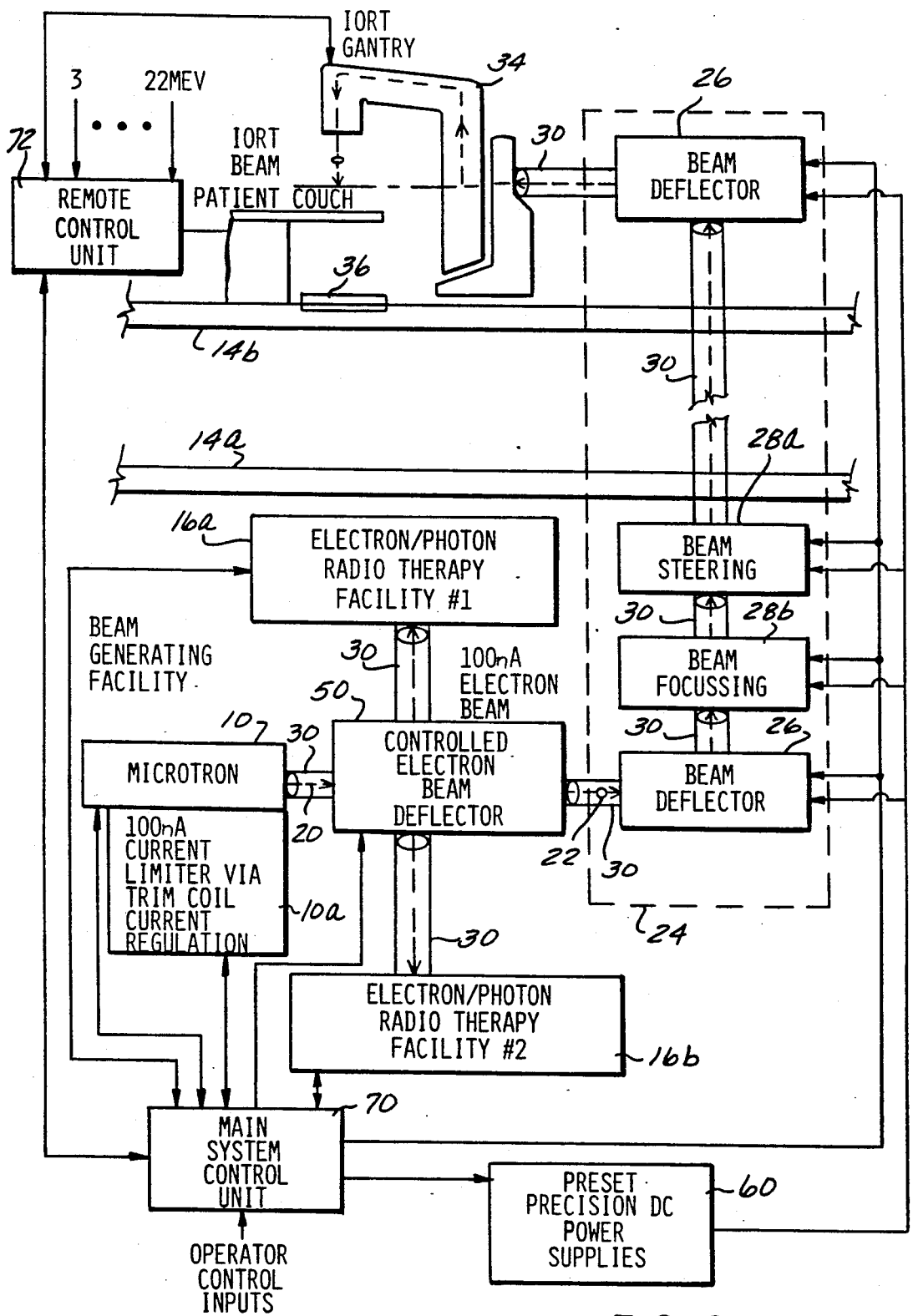

These as well as other objects and advantages of this invention will be more completely appreciated and understood by carefully studying the following detailed description of a presently preferred exemplary embodiment of this invention when taken in conjunction with the accompanying drawings, of which:

FIG. 1 is a partially cut-away schematic view of a multi-story radiation therapy system including an IORT treatment unit remotely located from the electron beam generating apparatus; and FIG. 2 is a more detailed schematic diagram of the system shown in FIG. 1 including a block diagram of suitable system elements and controls.

As shown in FIG. 1, a conventional 22 MeV microtron 10 is disposed on the lowest or basement level 12 of a multi-story building 14. One or more conventional photon/electron therapy units 16 is typically also provided near the microtron 10 in one or more rooms which are heavily shielded (e.g., with thick concrete/steel/lead enclosures 18). This much of the system is conventional.

In addition, in accordance with this invention, the output electron beam 20 from microtron 10 may be selectively routed along path 22 via an extended beam transport system 24 which includes conventional beam deflectors 26 (e.g., 90°) and conventional beam focusing and steering units 28 suitably distributed along the extended beam transport system so as to maintain the beam properly focused and located within the center of an evacuated piping system 30 as will be apparent to those in the art. The electron beam 32 exiting from the distal end of the beam transport system is directed coincidentally along the isocenter rotational axis of the gantry of a IORT treatment unit 34 (e.g., located on an upper floor in an operating suite of building 14). Only relatively minimal shielding (e.g., lead shield 36 located in the floor under the exit port of the IORT treatment unit 34 and minimal concrete shielding between the opera room and hallway wall) need be provided in the operating suite itself in addition to rather minimal shielding requirements along the beam transport system itself (e.g., an 80 mm thick lead sheath) and within the gantry 34 such as will be appreciated by those in the art.

A more complete depiction of the exemplary system is shown schematically in FIG. 2. The electron beam 20 output from microtron 10 is conventionally collimated by a set of graphite blocks positioned adjacent to the standard extraction tube (not shown). This defines the emittance of the beam to a value matching the acceptance requirements of the stationary beam transport system. A controlled electron beam deflector 50 includes conventional bending magnets, beam focusing and beam steering elements so as to selectively deflect electron beam 20 to either of electron/photon radiotherapy facilities 16A, 16B or to the remote beam transport system 24. For example, the controlled electron beam deflector 50 may include a 90° achromatic deflection system having two 45° bending magnets with a single quadrupole positioned in the plane of symmetry so as to direct the beam to the standard rotating electron/photon radiotherapy gantry 16A. The first 45° bending magnet may, for example, also include a straight-through port so as to permit the beam to be switched to the transport system 24 connecting with the special oncology surgery suite located at a remote site on floor 14B of building 14. Similar controlled beam steering arrangements may be used for alternatively deflecting the beam to the electron/photon radiotherapy unit 16B as will be appreciated.

The remote beam transport system 24 includes suitable conventional beam deflectors 26, beam focusing units 28B and beam steering units 28A so as to maintain the electron beam approximately centered within the evacuated piping system 30. As will be appreciated, such beam deflector, focusing and steering units should be distributed as necessary along the extended length of the remote beam transport system (which may, for example, extend from as little as about 20 feet to as much as about 100 feet in the exemplary embodiment). In one particular arrangement, the remote beam transport system utilizes four 90° deflection magnets directing the beam first upward for a distance of 5 feet and then horizontally for a distance of 17 feet, then vertically again for a distance of 43 feet and, finally, horizontally again along the isocenter axis of the remote IORT electron beam treatment facility gantry 34 (which gantry need have only a fairly limited isocentric arc travel of ±45°). A quadrupole triplet may be positioned, for example, between the second and third 90° bending magnets and 3 additional quadrupole triplets may be distributed along the 43 foot vertical rise so as to maintain proper beam focus. Six steering magnets may also be positioned as necessary along the transport line so as to permit periodic adjustment of beam position within the pipe 30 in both cross-dimensional coordinates. Precision d.c. power supplies 60 may be pre-programmed for each available energy setting (e.g., ten different energy settings ranging from 3 to 22 MeV) so as to maintain the correct field conditions in each of the distributed beam transport line elements 26, 28A and 28B.

In each of the conventional rotating gantries of electron/photon radiotherapy facilities 16A, 16B as well as in the optimized IORT gantry 34, the electron beam is conventionally brought to the treatment head by electron beam optical elements mounted within the gantry arms. For example, after entering the gantry along the isocenter axis of rotation, a 90° bending magnet may be used to deflect the beam 90° away from the rotational axis (e.g., as shown by the vertical dotted line in gantry 34) and then caused to make a broad U-turn back towards intersection with the isocenter rotational axis by two additional bending magnets of 82° and 98° respectively. Conventional quadrupole magnets may be used for focusing and conventional deflection coils may be provided for beam positioning as should be appreciated. It is, of course, assumed that the beam enters the treatment head on the rotational axis of the collimating system.

Typically, the beam may be focused conventionally at the entrance of the treatment head to a diameter of approximately 2 millimeters with an angular divergence of about 5°. This focus may be obtained by adjustments to the last 98° bending magnet and to the final quadrupole triplet. It is typically located just outside a vacuum window at a distance of about 100 cm from the isocenter so as to act as the primary radiation source during electron therapy with primary scattering foils in place (and in the case of the radiotherapy facility 16A, 16B, for photon therapy with a suitable target in place).

Also conventionally included with such treatment heads are two electrically independent multi-section open air transmission ionization chambers (not shown), each having an independent voltage supply and electronics. The two dose monitoring systems are arranged as a redundant dose monitoring combination. The ionization chambers are mounted after the primary collimator and flattening filters (not shown) but before the wedge filters (not shown) The detectors are pressure and temperature compensated and positioned at 90° relative rotations with respect to each other in the longitudinal and transverse field. Radiation field symmetry specifications may be maintained by a conventional servo system which senses and compares signal levels in both longitudinal and transverse fields and corrects a beam spot position by regulating the rotating gantry steering coils. Such conventional field symmetry servo systems are typically stable within 5 to 10 seconds after commencement of a treatment plan. Accordingly, within this response time, the beam is accurately transported by using pre-set control parameters associated with the remote transport system 34 as previously mentioned.

The ionization chambers, also control "dose rate" in the electron mode through a conventional servo system which regulates microtron trim coil current and thus determines the amount of electron beam current that passes through the microtron extraction tube. In the electron beam therapy mode used for the remotely located IORT gantry 34, the output current for microtron 10 is limited to about 100 nonoamperes by such control of the microtron trim coil 10A.

Such a simple beam transport geometry for the beam transport system 24 and for the IORT gantry 34 is possible because of the very narrow energy spread of the microtron electron beam output which relaxes requirements for achromatic optical systems. It is therefore possible to use simple and compact 90° bending magnets to focus the beam on the target in the IORT gantry 34 without obtaining asymmetry in the radiation field.

As will be appreciated by those in the art, the complete beam transport system will typically also include one or more auxiliary vacuum pumps, necessary vacuum hardware, radiation shields over the vacuum components and an area radiation monitoring system to prevent accelerator operation in an unsafe mode.

Typically, overall control of the entire facility will be achieved by a main system control unit 70 which is responsive to local operator control inputs as well as via remote control units such as remote control unit 72 located near the IORT gantry 34. Such control units may, for example, be partly or wholly "hardwired" or may, perhaps more typically include programmed computer controls. Since the required software for such controls is essentially unaltered from conventional installations (except, of course, as may be required to test for proper microtron operation from a remote location 72 and to then to remotely activate the 100 nanoampere current limit feature 10A, the controlled electron beam deflector 50 so as to direct the beam into the remote beam transport system 24 and proper activation of preset precision d.c. power supply 60 so as to provide the distributed active elements of the remote beam transport system with d.c. power levels suitable for properly transporting an electron beam of the chosen energy level (e.g., 1 of 10 discrete levels from 3 to 22 MeV). Since these few added control features for the alternate IORT mode of operation are believed well within the capabilities of those ordinarily skilled in the design of these facilities, no more detailed description is believed necessary.

As will be appreciated in view of the above-discussion, the exemplary embodiment permits a virtually ideally optimized IORT facility to be located directly in an operating suite. Depth dose, surface dose, electron field size, dose rate and gantry angles may all be specifically optimized for IORT in such a system. Evaluation of the true potential of IORT requires a technical system which makes this modality practical and convenient for the surgeon, radiation oncologist and patient alike. The exemplary embodiment described above represents a practical and economic solution to this problem which facilitates utilization and promotes patient accrual without the associated risks of patient transportation, prolonged anesthesia and pre-selection requiring a second operative procedure.

Although only one exemplary embodiment has been described in detail, those skilled in the art will understand that many variations and modifications may be made in this exemplary embodiment while yet maintaining many of the novel features and advantages of this invention. Accordingly, all such modifications and variations are intended to be included within the scope of the following claims.

What is claimed is:

1. A method for alternatively utilizing a single microtron for time shared intraoperative and conventional radiotherapy at alternate sites in a multilevel building having an operating suite level and a radiation therapy level, comprising the steps of:

generating an electron beam with said microtron of selectively variable current and energy levels;

generating an electron beam at a current level high enough to enable a full range of radiotherapy, including effective photon irradiation, to a treatment site located on said radio-therapy level in said building, and transporting said high current electron beam over a transport system adapted to provide adequate shielding for said high current level electron beam;

alternatively generating an electron beam having a current level high enough at a maximum for effective electron beam treatment, but substantially below the current level required for effective photon radiotherapy, and transporting said low current level beam over a relatively lightly shielded transport system to a treatment head located within an laternate site comprising a conventional operating suite on said operating suite level in said building, isolated and remote from said conventional treatment site and said microtron, whereby said microtron can be utilized for a complete range of conventional treatment at said conventional treatment site on said radiotheraphy level in said building and alternatively exclusively for intraoperative therapy at an alternate site comprised of an operating suite on said operating suite level in said building whereat said intraoperative therapy can be performed without moving patient out of said operating suite.

2. A method for alternatively utilizing s single microtron for time shared intraoperative and conventional radiotherapy at alternate sites, comprising the steps of:

generating an electron beam with said microtron of selectively variable current and energy levels;

generating an electron beam at a current level high enough to enable a full range of radiotherapy, including effective photon irradiation, to a conventional treatment site, and transporting said high current electron beam over a transport system adapted to provide adequate shielding for said high current level electron beam;

performing photon irradiation on patients at said conventional treatment site;

alternatively generating an electron beam having a current level high enough at a maximum for effective electron beam treatment, but substantially below the current level required for effective photon radiotherapy, and transporting said low current level beam over a relatively lightly shielded transport system to a treatment head located within an alternate site comprising a conventional operating suite, isolated and remote from said conventional treatment site and said microtron, said conventional operating suite equipped and isolated to be adapted for the performance of all surgical procedures required therein;

performing surgery on patients at said alternate site to expose irradiation treatment areas within said patients;

directing electron beam irradiation onto said treatment areas from said treatment head;

3. The method according to claim 2 wherein said low current level electron beam is limited to have a maximum current level of approximately 100 nanoamperes.

* * * * *

UNITED STATES PATENT AND TRADEMARK OFFICE
CERTIFICATE OF CORRECTION

PATENT NO. : 5,190,516

DATED : March 2, 1993

INVENTOR(S) : Donald G. Bronn

It is certified that error appears in the above-identified patent and that said Letters Patent is hereby corrected as shown below:

On title page, item [54], and col. 1, lines 1-3, in the title;

"METHOD INTRAOPERATIVE ELECTRON BEAM RADIOTHERAPY USING REMOTELY LOCATED BEAM GENERATOR" should be --METHOD FOR INTRAOPERATIVE ELECTRON BEAM RADIOTHERAPY USING REMOTELY LOCATED BEAM GENERATOR--

IN THE CLAIMS

Column 10, line 41 (Claim 2), during printing, the following paragraph was omitted. After "head;", please insert:

--thereafter performing surgery while said patients are at said alternate site to close up said treatment areas, whereby said microtron can be utilized for a complete range of conventional treatment at said conventional treatment site and alternatively exclusively for intraoperative therapy at an alternate site comprised of an operating room whereat said surgery and intraoperative therapy

UNITED STATES PATENT AND TRADEMARK OFFICE
CERTIFICATE OF CORRECTION

PATENT NO. : 5,190,516
DATED : March 2, 1993
INVENTOR(S) : Donald G. Bronn

It is certified that error appears in the above-indentified patent and that said Letters Patent is hereby corrected as shown below:

can be completely performed without moving a patient out of said operating room.--

Signed and Sealed this

Eighteenth Day of January, 1994

Attest:

BRUCE LEHMAN

Attesting Officer　　　Commissioner of Patents and Trademarks